United States Patent
Hamed

(10) Patent No.: US 7,312,297 B2
(45) Date of Patent: Dec. 25, 2007

(54) TREATMENT COMPOSITION FOR MAKING ACQUISITION FLUFF PULP IN SHEET FORM

(75) Inventor: Othman A. Hamed, Jesup, GA (US)

(73) Assignee: Rayonier TRS Holdings, Inc., Jesup, GA (US)

( * ) Notice: Subject to any disclaimer, the term of this patent is extended or adjusted under 35 U.S.C. 154(b) by 0 days.

(21) Appl. No.: 11/058,213

(22) Filed: Feb. 16, 2005

(65) Prior Publication Data

US 2006/0184147 A1    Aug. 17, 2006

(51) Int. Cl.
*D06M 13/322*    (2006.01)

(52) U.S. Cl. .......................... 528/38; 528/26; 528/28; 528/25; 252/182.3; 252/182.14; 8/188; 8/DIG. 1

(58) Field of Classification Search .................. 528/38, 528/26, 25, 28; 252/182.3, 182.14; 8/188, 8/DIG. 1
See application file for complete search history.

(56) References Cited

U.S. PATENT DOCUMENTS

| 3,224,926 | A | | 12/1965 | Bernardin |
| 3,241,553 | A | | 3/1966 | Steiger |
| 3,434,918 | A | | 3/1969 | Bernardin |
| 3,700,549 | A | | 10/1972 | Croon et al. |
| 3,844,880 | A | | 10/1974 | Meisel, Jr. et al. |
| 3,932,209 | A | | 1/1976 | Chatterjee |
| 4,204,054 | A | | 5/1980 | Lesas et al. |
| 5,393,330 | A | * | 2/1995 | Chen et al. .................... 106/2 |
| 5,399,240 | A | | 3/1995 | Graef et al. |
| 5,614,570 | A | | 3/1997 | Hansen et al. |
| 5,637,295 | A | * | 6/1997 | Lang et al. ................ 424/70.2 |
| 5,741,765 | A | * | 4/1998 | Leach ........................ 510/123 |
| 5,965,466 | A | | 10/1999 | Rodrigues et al. |
| 6,258,367 | B1 | * | 7/2001 | Dupuis ...................... 424/401 |
| 6,290,867 | B1 | | 9/2001 | Kielbania, Jr. et al. |
| 6,464,730 | B1 | * | 10/2002 | Login et al. ................. 8/116.1 |
| 6,605,666 | B1 | * | 8/2003 | Scholz et al. ............... 524/591 |
| 2005/0079361 | A1 | | 4/2005 | Hamed et al. |

FOREIGN PATENT DOCUMENTS

EP    0 427 316    5/1991

OTHER PUBLICATIONS

*Intrn'l Search Report* and Written Opinion for PCT/US06/05417, Oct. 19, 2006.

* cited by examiner

*Primary Examiner*—Margaret G. Moore
(74) *Attorney, Agent, or Firm*—Hunton & Williams LLP

(57) ABSTRACT

A treatment composition for making acquisition fluff pulp in sheet form, having a cross-linking agent and an anti-hydrogen-bonding agent. The cross-linking agent may be a polycarboxylic acid, aldehyde, urea-based derivatives or a mixture thereof. The anti-hydrogen-bonding agent may be a silicon polymer terminated with at least one quaternary amine functional group. A method of making acquisition fluff pulp using the treatment composition involves treating a cellulosic base fiber with a treatment composition solution to impregnate the fiber with the treatment composition, and then drying and curing the impregnated fiber. The resultant acquisition fluff pulp may be utilized in an acquisition layer and/or an absorbent core of an absorbent article intended for body waste management.

32 Claims, No Drawings

TREATMENT COMPOSITION FOR MAKING ACQUISITION FLUFF PULP IN SHEET FORM

BACKGROUND

1. Field

Embodiments of the invention relate to a treatment composition containing a mixture of a cross-linking agent and an anti-hydrogen-bonding agent for making acquisition fluff pulp with low centrifuge retention capacity in sheet form. Embodiments of the present invention also relate to a process for making the acquisition fluff pulp in sheet form. The fluff pulp can be characterized as having improved resiliency, bulk, and acquisition rate, which makes it suitable for use in an acquisition layer of absorbent articles intended for body fluid management.

2. Description of Related Art

Absorbent articles intended for personal care, such as adult incontinent pads, feminine care products, and infant diapers typically are comprised of at least a top sheet, a back sheet, an absorbent core positioned between the top sheet and back sheet, and an optional acquisition/distribution layer positioned between the top sheet and the absorbent core. An acquisition/distribution layer usually is incorporated in the absorbent articles to provide better distribution of liquid, increased rate of liquid absorption, reduced gel blocking, and improved surface dryness. The acquisition/distribution layer may be comprised of, for example, synthetic fibers, a composite of cellulosic fibers and synthetic fibers, or cross-linked cellulosic fibers. Cross-linked cellulosic fiber is preferred because it is abundant, it is biodegradable, and it is relatively inexpensive.

Cross-linked cellulosic fibers and processes for making them have been described in the literature for many years (see, for example, G. C. Tesoro, *Cross-Linking of Cellulosics*, in Vol. II of Handbook of Fiber Science and Technology, pp. 1–46 (M. Lewin and S. B. Sello eds., Mercel Dekker, New York, 1983)). The cross-linked cellulosic fibers typically are prepared by reacting cellulose with polyfunctional agents that are capable of covalently bonding to at least two hydroxyl groups of the anhydroglucose repeat unit of cellulose in neighboring chains simultaneously.

Cellulosic fibers typically are cross-linked in fluff form. Processes for making cross-linked fiber in fluff form comprise dipping swollen or non-swollen fiber in an aqueous solution of cross-linking agent and a catalyst. The fiber so treated, then is usually cross-linked by heating it at elevated temperature in the swollen state, as described in U.S. Pat. No. 3,241,553, or in the collapsed state after defiberizing it, as described in U.S. Pat. No. 3,224,926, and European Patent No. 0,427,361 B1, the disclosures of each of which are incorporated by reference herein in their entirety.

Cross-linking of fibers is believed to improve the physical and the chemical properties of fibers in many ways, such as improving the fibers' wet and dry resiliency, increasing fluid absorbency, reducing wrinkling, and improving shrinkage resistance. However, cross-linked cellulosic fibers have not been widely adopted in absorbent products, seemingly because of the difficulty of making cross-linked cellulosic fibers in sheet form. More specifically, it has been found that cross-linked fiber in the sheet form tends to create substantial problems when defiberized. These problems include severe fiber breakage and increased amounts of knots and nits (hard fiber clumps). Furthermore, such cross-linked fibers demonstrate an unpleasant odor and low fiber brightness. These problems render the cross-linked fiber unsuitable for applications in absorbent articles intended for body waste managements.

The difficulties associated with defiberizing fibers cross-linked in sheet form were attributed to the considerable amount of lignin and hemicellulose that remains in the fiber after the pulping and bleaching processes. Large portions of these residuals are distributed on the surfaces of the fibers. These residuals under the heating conditions of the cross-linking reaction combine with the cross-linking agents to form thermosetting adhesives. As a result, strong bonding forms between adjacent fibers so that it is very difficult to separate them under any conditions without considerable fiber breakage. Because the cross-linked fibers tend to be brittle, the fibers themselves will often break, generating fibers with high contents of knots, nits and fines.

Efforts to make cross-linked fibers in sheet form have met with limited success. Some attempts have involved minimizing the contact between fibers in the sheet then cross-link the fibers. For example, Graef et al. in U.S. Pat. No. 5,399,240, the disclosure of which is incorporated herein by reference in its entirety, discloses a method of making a sheet of fibers containing a de-bonding agent, followed by treating the sheet while in the wet state with a mixture of a cross-linking agent and a catalyst. The de-bonder used is composed of a fatty chain and quaternary ammonium group. The fatty chain tends to interfere with the hydrogen bonding between fibers during sheet formation. This reduction in hydrogen bonding leads to a softer and partially bonded sheet of fluff pulp. While in sheet form, the fiber is then cured at elevated temperatures to produce cross-linked fibers with a relatively low content of knots and nits. Unfortunately, the long hydrophobic alkane chain tends to adversely affect the absorbency and wettability of the fiber, rendering it unsuitable for applications such as in absorbent articles, where a high rate of absorbency and fast acquisition are essential.

In U.S. Pat. No. 3,434,918, Bernardin et al. discloses a method of treating fibers in sheet form with a cross-linking agent and a catalyst. The treated sheet then is wet-aged to render the cross-linking agent non-extractable. The wet-aged fibers are re-dispersed before curing, mixed with untreated fibers, sheeted, and then cured. The mixture of cross-linked fibers and untreated fibers are potentially useful for making products such as filter media, tissues, and toweling where high bulk and good water absorbency are desired without excessive stiffness in the product. Unfortunately, the presence of untreated fibers make the produced fibers have low performance as an acquisition/distribution layer in hygiene products such as diapers.

Other documents describing methods of treating fiber in sheet form include, for example, U.S. Pat. Nos. 4,204,054; 3,844,880; and 3,700,549 (the disclosures of each of which are incorporated by reference herein in their entirety). However, the above-described approaches complicate the process of cross-linking fiber in sheet form, and render the process time consuming, and costly. In addition to that, these processes result in cross-linked fibers with a substantial decrease in fiber performance, and a substantial increase in cost.

In order to avoid such problems, Chatterjee, et al., showed in U.S. Pat. No. 3,932,209 (the disclosure of which is incorporated herein by reference in its entirety) that mercerized fiber having low contents of hemicellulose and lignin can be cross-linked in sheet form without substantial formation of knots and nits. Unfortunately, the use of mercerized fiber to produce cross-linked fiber in sheet form is relatively expensive.

In previous work, (e.g., U.S. patent application Ser. No. 10/683,164 entitled "Materials Useful In Making Cellulosic Acquisition Fibers In Sheet Form" filed Oct. 10, 2003, the disclosure of which is incorporated herein by reference in its entirety) it was shown that conventional fibers can be successfully cross-linked in sheet form using modified cross-linking agents. The modified cross-linking agent acts as a cross-linking agent and as a wedge that lowers the inter-fiber bonding and increase fiber bulkiness. This way, the formation of knots and nits as well as fines during fiber cross-linking were minimized. The produced cross-linked fibers showed similar or better performance characteristics than conventional individualized cross-linked cellulose fibers.

The description herein of certain advantages and disadvantages of known cellulosic fibers, treatment compositions, and methods of their preparation, is not intended to limit the scope of the embodiments. Indeed, the embodiments may include some or all of the methods, fibers and compositions described above without suffering from the same disadvantages.

SUMMARY

In view of the difficulties presented by cross-linking cellulosic fibers in the sheet form, there remains a need for a simple, relatively inexpensive, treatment composition suitable for making acquisition fluff pulp in sheet form without sacrificing wettability of the fibers, whereby the resultant sheet can be defiberized into individual fibers without serious fiber breakage. The resultant sheet also preferably has low contents of knots and nits, and reduced odor and discoloration. There also exists a need for a process of making acquisition fluff pulp in sheet form that provides time and cost savings to both the fiber producer and the manufacturer of absorbent articles. Embodiments of the invention attempt to fulfill these needs and to provide further related advantages.

It is therefore a feature of an embodiment of the invention to provide a treatment composition to be used in making acquisition fluff pulp in sheet form. The treatment composition comprises a mixture of a cross-linking agent and an anti-hydrogen-bonding agent.

In another embodiment of the invention, a method for making acquisition fluff pulp of the present invention is provided. The method involves providing a treatment composition solution that comprises the treatment composition described above, providing a cellulosic base fiber in sheet form, and applying the treatment composition solution to the cellulosic base fiber to impregnate the sheet of fluff pulp with the treatment composition, and thereafter drying and curing the impregnated sheet to produce acquisition fluff pulp in sheet form.

It also is a feature of an embodiment of the present invention to provide an acquisition fluff pulp made by the above-described method. It also is a feature of an embodiment of the present invention to provide an absorbent article comprising the acquisition fluff pulp.

These and other objects, features and advantages of the present invention will appear more fully from the following detailed description of the preferred embodiments of the invention.

DETAILED DESCRIPTION OF PREFERRED EMBODIMENTS

Embodiments of the present invention are directed to an acquisition fluff pulp in sheet form, to a method of making the acquisition fluff pulp, and to a treatment composition for use in the method of making the fluff pulp. The method comprises treating the cellulosic fibers in sheet or roll form with an aqueous solution of a treatment composition described in the embodiments and then drying and curing the treated fibers.

The acquisition fluff pulp of embodiments of the present invention is useful in absorbent articles, and in particular, is useful in forming acquisition/distribution layers or absorbent cores in absorbent articles. The particular construction of the absorbent article is not critical to the present invention, and any absorbent article can benefit from this invention. Suitable absorbent garments are described, for example, in U.S. Pat. Nos. 5,281,207, and 6,068,620, the disclosures of each of which are incorporated by reference herein in their entirety including their respective drawings. Those skilled in the art will be capable of utilizing acquisition fluff pulp of the present invention in absorbent garments, cores, acquisition layers, and the like, using the guidelines provided herein.

As used herein, the terms and phrases "absorbent garment," "absorbent article" or simply "article" or "garment" refer to mechanisms that absorb and contain body fluids and other body exudates. More specifically, these terms refer to garments that are placed against or in proximity to the body of a wearer to absorb and contain the various exudates discharged from the body. A non-exhaustive list of examples of absorbent garments includes diapers, diaper covers, disposable diapers, training pants, feminine hygiene products and adult incontinence products. Such garments may be intended to be discarded or partially discarded after a single use ("disposable" garments). Such garments may comprise essentially a single inseparable structure ("unitary" garments), or they may comprise replaceable inserts or other interchangeable parts.

Embodiments of the present invention may be used with all of the foregoing classes of absorbent garments, without limitation, whether disposable or otherwise. Some of the embodiments described herein provide, as an exemplary structure, a diaper for an infant, however this is not intended to limit the claimed invention. The invention will be understood to encompass, without limitation, all classes and types of absorbent garments, including those described herein.

The term "component" can refer, but is not limited, to designated selected regions, such as edges, corners, sides or the like; structural members, such as elastic strips, absorbent pads, stretchable layers or panels, layers of material, or the like.

Throughout this description, the term "disposed" and the expressions "disposed on," "disposed above," "disposed below," "disposing on," "disposed in," "disposed between" and variations thereof are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Throughout this description, the phrases "top sheet" and "back sheet" denote the relationship of these materials or layers with respect to the absorbent core. It is understood that additional layers may be present between the absorbent core and the top sheet and back sheet, and that additional layers and other materials may be present on the side opposite the absorbent core from either the top sheet or the back sheet.

Throughout this description, the expressions "upper layer," "lower layer," "above" and "below," which refer to the various components included in the absorbent material are used to describe the spatial relationship between the respective components. The upper layer or component "above" the other component need not always remain vertically above the core or component, and the lower layer or component "below" the other component need not always remain vertically below the core or component. Other configurations are contemplated within the context of the present invention.

Throughout this description, the term "impregnated" insofar as it relates to a treatment composition impregnated a fiber, denotes an intimate mixture of treatment composition and cellulosic fiber, whereby the treatment composition may be adhered to the fibers, adsorbed on the surface of the fibers, or linked via chemical, hydrogen or other bonding (e.g., Van der Waals forces) to the fibers. Impregnated in the context of the embodiments does not necessarily mean that the treatment composition is physically positioned beneath the surface of the fibers.

Throughout this description, the expression "acquisition fiber" as used herein refers to a cross-linked cellulosic fiber suitable for use in the acquisition/distribution layer of an absorbent article intended for body waste management. The acquisition fiber tends to impart bulk and resilience to the layer and tends to provide the layer with a generally open structure that rapidly transfers liquid away from the point of insult, and distributes it over a large area in the storage layer.

In accordance with embodiments of the present invention, the treatment composition that is useful in making acquisition fluff pulp in sheet form is a mixture of cross-linking agent and an anti-hydrogen-bonding agent. The treatment composition may be prepared by any suitable and convenient procedure. The cross-linking agent and the anti-hydrogen-bonding agent preferably are mixed in a weight ratio of cross-linking agent to anti-hydrogen-bonding agent of from about 1:1 to about 100:1, and more preferably from about 1:1 to 50:1. Preferably, the treatment composition is present in an aqueous solution, diluted with water to a pre-determined concentration.

Any cross-linking agent known in the art that is capable of cross-linking cellulosic fibers can be used in the treatment composition. Suitable cross-linking agents include, for example, alkane polycarboxylic acids, polymeric polycarboxylic acids, aldehydes, and urea-based derivatives. Suitable alkane polycarboxylic acids include, for example, aliphatic and alicyclic polycarboxylic acids containing at least two carboxylic acid groups. The aliphatic and alicyclic polycarboxylic acids could be either saturated or unsaturated, and they might also contain other heteroatoms such as sulfur, nitrogen or halogen. Examples of suitable polycarboxylic acids include: 1,2,3,4-butanetetracarboxylic acid, 1,2,3-propanetricarboxylic acid, oxydisuccinic acid, citric acid, itaconic acid, maleic acid, tartaric acid, glutaric acid, iminodiacetic acid, citraconic acid, tartrate monosuccinic acid, benzene hexacarboxylic acid, cyclohexanehexacarboxylic acid, maleic acid, and any combinations or mixtures thereof.

Suitable polymeric polycarboxylic acid cross-linking agents include, for example, those formed from monomers and/or co-monomers that contain carboxylic acid groups or functional groups that can be converted into carboxylic acid groups. Such monomers include, for example, acrylic acid, vinyl acetate, maleic acid, maleic anhydride, carboxy ethyl acrylate, itanoic acid, fumaric acid, methacrylic acid, crotonic acid, aconitic acid, tartrate monosuccinic acid, acrylic acid ester, methacrylic acid ester, acrylic amide, methacrylic amide, butadiene, styrene, or any combinations or mixtures thereof.

Examples of suitable polymeric polycarboxylic acids include polyacrylic acid and polyacrylic acid copolymers such as, for example, poly(acrylamide-co-acrylic acid), poly(acrylic acid-co-maleic acid), poly(ethylene-co-acrylic acid), and poly(1-vinylpyrolidone-co-acrylic acid), as well as other polyacrylic acid derivatives such as poly(ethylene-co-methacrylic acid) and poly(methyl methacrylate-co-methacrylic acid). Other examples of suitable polymeric polycarboxylic acids include polymaleic acid and polymaleic acid copolymers such as, for example, poly(methyl vinyl ether-co-maleic acid), poly(styrene-co-maleic acid), and poly(vinyl chloride-co-vinyl acetate-co-maleic acid). The representative polycarboxylic acid copolymers noted above are commercially available in various molecular weights.

Suitable aldehyde cross-linking agents include, for example, formaldehyde, glyoxal, glutaraldehyde, glyoxylic acid and glyceraldehydes. Suitable urea-based derivatives for use in the present invention include, for example, urea based-formaldehyde addition products, such as, for example, methylolated ureas, methylolated cyclic ureas, methylolated lower alkyl cyclic ureas, methylolated dihydroxy cyclic ureas, dihydroxy cyclic ureas, and lower alkyl substituted cyclic ureas. Especially preferred urea-based crosslinking agents include dimethyldihydroxy urea (DM-DHU, or 1,3-dimethyl-4,5-dihydroxy-2-imidazolidinone), dimethyloldihydroxyethylene urea (DMDHEU, or 1,3-dihydroxymethyl-4,5-dihydroxy-2-imidazolidinone), dimethylol urea (DMU, or bis[N-hydroxymethyl]urea), dihydroxyethylene urea (DHEU, or 4,5-dihydroxy-2-imidazolidinone), dimethylolethylene urea (DMEU, or 1,3-dihydroxymethyl-2-imidazolidinone), and dimethyldihydroxyethylene urea (DDI, or 4,5-dihydroxy-1,3-dimethyl-2-imidazolidinone). Other suitable substituted ureas include glyoxal adducts of ureas, polyhydroxyalkyl urea disclosed in U.S. Pat. No. 6,290,867, and hydroxyalkyl urea and β-hydroxyalkyl amide disclosed in U.S. Pat. No. 5,965,466.

Alternatively, a cross-linking agent suitable for use in the embodiments may be comprised of any combination or mixture of two or more of the above mentioned cross-linking agents.

The phrase "anti-hydrogen-bonding agent" or "silicon-based anti-hydrogen-bonding agent" as used herein refers to quaternary ammonium terminated polysiloxanes that are water soluble or water dispersible, and that are able to alter the formation of hydrogen bonding among cellulosic fibers when sheeted and compressed. Examples of anti-hydrogen-bonding agents suitable for use in the treatment composition preferably are represented by Formulas I and II below.

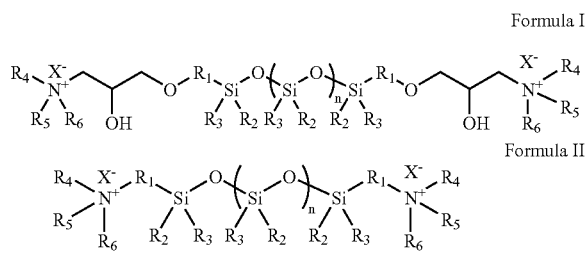

Formula I

Formula II

In Formulas I and II, $R_1$ represents a divalent alky group with two or more carbon atoms that can be branched or cyclic. Optionally $R_1$ can be a polyether or co-polyether substituted with one or more hydroxyl groups. $R_2$ and $R_3$, each independently represent an alkyl group with one or more carbon atoms that can be branched or cyclic, where preferably at least one of the alky groups is a polyether group or co-polyether terminated with a hydroxyl group. $R_4$ to $R_6$ each independently represent a hydrogen atom or an organic group, where the organic group is an alkyl, aryl, alkoxy, alkaryl substituted alkyl, cycloaliphatic, aromatic, or a mixture thereof, and together R4 to R6 can form a cyclic or aromatic ring. Preferably at least one of these organic groups is hydroxyl terminated. In Formulas I and II, X represents an anion, such as a halogen ion, an organic carboxylate, hydroxyl, or a compound with general Formula of $RSO_3$—. In Formulas I and II, "n" represents the number of repeating units in the polymer chain, and is a number from 10 to 200.

Quaternary ammonium terminated polysiloxanes characterized by Formula I can be synthesized as shown in Scheme I below by reacting an epoxy terminated polysiloxane with organic amines. Examples of epoxy terminated polysiloxanes include poly(dimethylsiloxane), diglycidyl ether terminated. Any organic amines that are aliphatic linear, branched or cyclic amines containing at least one primary, secondary or tertiary amino group can be used in the present invention. Preferably the amines are polyamines terminated with only one amine group. More preferably, the amines are secondary and containing at least one hydroxyl group. Examples of organic amines suitable for use in the present invention include but are not limited to diethylamine, ethanolamine, diethanolamine, bis-2-hydroxypropylamine, bis-3-hydroxypropylamine, triethanolamine, tris-2-hydroxypropylamine, N-methylethanolamine, N-benzylethanolamine, N,N-dimethylethanolamine, piperidine, and morpholine. Primary amines and polyamines tend to form with poly(dimethylsiloxane), diglycidyl ether terminated cross-linked three-dimensional polymer which is insoluble in any solvent.

In an embodiment of the invention, the organic amine and epoxy terminated polysiloxane, respectively, are preferably employed in an equivalent ratio of about 1.0 to 2.0. As used herein, the expression "equivalent ratio" means the ratio of the equivalent weight of organic amine to the equivalent weight of epoxy terminated polysiloxane. The equivalent weight of the amine is equal to the molecular weight of the amine divided by the number of amine hydrogens. The equivalent weight of epoxy terminated polysiloxane is equal to the molecular weight of the epoxy divided by the number of epoxy groups.

The reaction between the amine and epoxy terminated polysiloxane preferably is conducted under an inert atmosphere of nitrogen at room temperature for overnight, and more preferably the reaction is conducted at 50° C. to about 100° C. for about six hours.

In a preferred embodiment of the invention, the organic amine is diethanol amine and the polysiloxane is poly (dimethylsiloxane), diglycidyl ether terminated. Scheme I shows a representative example for making quaternary ammonium terminated polysiloxane with Formula I by reacting diethanolamine with poly(dimethylsiloxane), diglycidyl ether terminated, in stoichiometric proportions based on equivalent weight, preferably with a slight excess of the diethanol amine present.

Scheme I

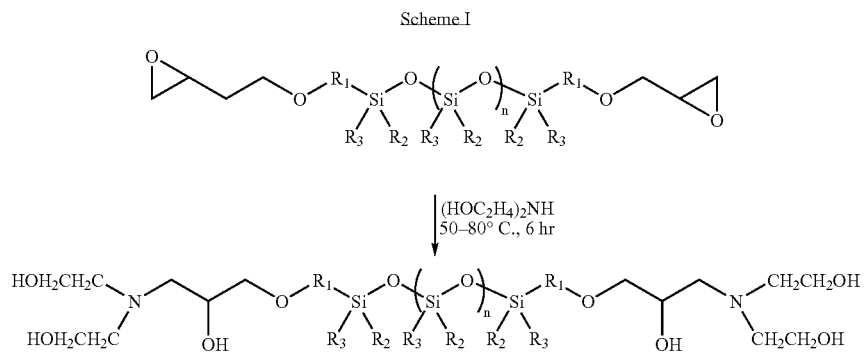

Suitable silicon polymer compounds with terminal amines shown in Formula II include poly(dimethylsiloxanebis[[3-[(2-aminoethyl)amino]propyl]dimethoxysilylether; poly(dimethylsiloxane), bis(3-aminopropyl) terminated; poly[dimethylsiloxane-co-(3-aminopropyl) methylsiloxane]; and the QUATERNIUM-80 marketed by Goldschmidt under the trademark Abil® Quat 3270, 3272, and 3474.

A silicon polymer compound terminated with amines can be converted into ammonium prior to mixing it with the cross-linking agent by treating it with an acid. Inorganic or organic acids are suitable for this purpose. Especially preferred acids include acetic acid, formic acid, phosphoric acid, citric acid, hydrochloric acid, glycolic acid, malic acid, lactic acid and glyoxylic acid. Preferably, the silicon polymer compound terminated with amines is used without acidification, since the acidification takes place upon mixing it with the polycarboxylic acid cross-linking agent to make the treatment composition solution of the present invention.

Without being limited to a specific theory, the quaternary ammonium terminated polysiloxane molecules appear to act as a debonder by virtue of the polysiloxane group, which disrupts the inter-fiber hydrogen bonding (fiber-to-fiber bonding)—as a result, voids are created among the fibers. These voids enhance the bulk of the fibers, thereby producing a softer and weaker sheet of cross-linked wood pulp which can be easily processed into individual fibers without excessive fiber breakage.

The quaternary ammonium terminated polysiloxane anti-hydrogen-bonding agents of the various embodiments are advantageous because they are soluble in acidic solution, and they are dispersible or soluble in water. In addition, only a small quantity of the anti-hydrogen-bonding agent is needed (as low as 0.05 wt % based on the fiber weight) in order to produce acquisition fluff pulp in sheet form which can be reprocessed into individual fibers without excessive fiber breakage. Unlike the conventional debonding agents, the quaternary ammonium terminated polysiloxane anti-hydrogen-bonding agents can be added to the fibers in sheet or slurry form, while in dry or wet state.

In addition to the above mentioned advantages, using the quaternary ammonium terminated polysiloxane in the treatment composition to make acquisition fluff pulp has shown no adverse effect on the acquisition properties of the acquisition fluff pulp.

The treatment composition of the embodiments may advantageously be used to make acquisition fluff pulp from conventional cellulosic fibers in sheet form. Acquisition fluff pulp made in sheet form in accordance with embodiments enjoy the same or better performance characteristics, when compared to conventional individualized cross-linked cellulose fibers, but avoids the processing problems associated with dusty individualized cross-linked fibers.

In addition to being more economical, there are several other advantages for making acquisition fluff pulp using the embodiments described herein, when compared to conventional cellulosic fibers in sheet form. Fibers cross-linked in sheet form have typically been expected to have an increased potential for inter-fiber cross-linking, which leads to "knots" and "nits" resulting in poor defiberization and performance. For instance, when a standard purity fluff pulp, Rayfloc®-J-LD, is cross-linked in sheet form with conventional cross-linking agents such as, for example, citric acid, the "knot" content increases substantially, indicating increased deleterious inter-fiber bonding (see Table 2). In contrast, the acquisition fluff pulp prepared in accordance with the embodiments preferably has less than about 30% of knots and nits, more preferably less than about 20% knots and nits, even more preferably less than about 15% knots and nits, and most preferably less than about 10% knots and nits. The acquisition fluff pulp described herein also preferably has less than about 10.0% of fines, preferably less than about 8.0% fines, and most preferably, less than about 7.0% fines. The acquisition fluff pulp of the embodiments also preferably has more than about 75% accepts.

Another embodiment of the present invention provides a method for making acquisition fluff pulp using the treatment composition of the present invention. The process preferably comprises treating cellulosic base fibers in sheet or roll form with an aqueous treatment composition solution to impregnate the cellulosic base fiber, followed by drying and curing the impregnated fiber at sufficient temperature and for a sufficient period of time to accelerate formation of covalent bonding between hydroxyl groups of cellulosic fibers and functional groups of the treatment composition.

The aqueous treatment composition solution comprises the treatment composition described above in the various embodiments. The treatment composition solution may be prepared by any suitable and convenient procedure. Preferably the treatment composition is present in the solution in a concentration of about 2.5 weight % to about 8.0 weight %, based on the total weight of the solution. Preferably the treatment composition is diluted to a concentration sufficient to provide from about 0.5 weight % to about 10.0 weight % of treatment composition on fiber, more preferably from about 2.0 weight % to about 7.0 weight %, and most preferably from about 3.0 weight % to about 6.0 weight %. By way of example, 7 weight % treatment composition is equal to 7 grams of treatment composition per 100 grams oven dried fiber. Preferably, the treatment composition solution according to embodiments of the present invention contains from about 0.005 weight % to about 5.0 weight %, and more preferably from about 0.01 weight % to 1.0 weight %, of the anti-hydrogen-bonding agent.

Preferably, the pH of the treatment composition solution is adjusted to from about 1 to about 5, more preferably from about 1.5 to about 3.5. The pH can be adjusted using alkaline solutions such as, for example, sodium hydroxide or sodium carbonate.

The treatment composition solution preferably includes a catalyst to accelerate the reaction between hydroxyl groups of cellulose and carboxyl groups of the cross-linking agent of the treatment composition of present invention. Any catalyst known in the art that is capable of accelerating the formation of an ester bond between hydroxyl groups and carboxylic acid groups may be used. Suitable catalysts include alkali metal salts of phosphorous containing acids such as alkali metal hypophosphites, alkali metal phosphites, alkali metal polyphosphonates, alkali metal phosphates, and alkali metal sulfonates. A particularly preferred catalyst is sodium hypophosphite. The catalyst can be applied to the fiber as a mixture with the treatment composition, before the addition of the treatment composition, or after the addition of treatment composition to the cellulosic fiber. A suitable weight ratio of catalyst to treatment composition is, for example from about 1:1 to about 1:10, and preferably from about 1:3 to about 1:6.

Optionally, the treatment composition solution may include other additives such as, for example, brighteners, odor absorbents and flame retardants. Examples of suitable flame retardant additives include, for example, sodium phosphate, ammonium hydrogen phosphate, boric acid, calcium chloride, ammonium sulfate, sodium bisulfate, sodium tetraborate decahydrate, sodium hydrogen phosphate, and ammonium carbonate.

Optionally, in addition to the treatment composition solution, other finishing agents such as softening and wetting agents also may be applied to the cellulosic base fiber. Examples of softening agents include fatty alcohols, fatty acids amides, polyglycol ethers, fatty alcohols sulfonates, and N-stearyl-urea compounds. Examples of wetting agents include fatty amines, salts of alkylnapthalenesulfonic acids, alkali metal salts of dioctyl sulfosuccinate, and the like.

The cellulosic base fiber may be any conventional or other cellulosic fiber, so long as it is capable of providing the desired physical characteristics described herein. Suitable cellulosic fiber for use in forming the acquisition fluff pulp includes that primarily derived from wood pulp. Suitable wood pulp can be obtained from any of the conventional chemical processes, such as the Kraft and sulfite processes.

Preferred fiber is that obtained from various soft wood pulp such as Southern pine, White pine, Caribbean pine, Western hemlock, various spruces, (e.g. Sitka Spruce), Douglas fir or mixtures and combinations thereof. Fiber obtained from hardwood pulp sources, such as gum, maple, oak, eucalyptus, poplar, beech, and aspen, or mixtures and combinations thereof also can be used in the embodiments. Other cellulosic fiber derived from cotton linter, bagasse, kemp, flax, and grass also may be used. The cellulosic base fiber can be comprised of a mixture of two or more of the foregoing cellulosic pulp products. Particularly preferred fibers for use in forming the acquisition fluff pulp are those derived from wood pulp prepared by the Kraft and sulfite-pulping processes. In addition, the cellulosic base fiber may be non-bleached, partially bleached or fully bleached cellulosic fiber.

The cellulosic base fibers can be provided in any of a variety of forms. For example, one aspect of the embodiments contemplates using cellulosic base fibers in sheet or roll form. In another aspect, the fiber can be provided in a mat of non-woven material. Fibers in mat form are not necessarily rolled up in a roll form, and typically have a density lower than fibers in sheet form. In yet another feature of an embodiment of the invention, the cellulosic base fiber is provided in a wet or dry state. It is preferred that the cellulosic base fibers be provided dry in a roll form.

The cellulosic base fiber that is treated in accordance with various embodiments while in the sheet form can be any of wood pulp fibers or fiber from any other source described previously. In one embodiment of the invention, fibers in the sheet form suitable for use in the embodiments include caustic-treated fibers.

Commercially available caustic extractive pulp suitable for use in the embodiments include, for example, Porosanier-J-HP, available from Rayonier Performance Fibers Division (Jesup, GA), and Buckeye's HPZ products, available from Buckeye Technologies (Perry, Fla.).

Any method of applying the treatment composition solution to the fiber in sheet form may be used, so long as it is capable of providing an effective amount of treatment composition to the fiber to produce the acquisition fluff pulp described herein. Preferably, the application method provides about 10% to about 150% by weight of solution to the fiber, based on the total weight of the fiber. Acceptable methods of application include, for example, spraying, dipping, impregnation, and the like. Preferably, the fiber is impregnated with the aqueous treatment composition solution. Impregnation typically creates a uniform distribution of treatment composition on the sheet and provides better penetration of treatment composition into the interior part of the sheet. Preferably, the treatment composition solution is applied to the cellulosic fibers to provide about 2% to about 7% by weight, and more preferably about 3% to about 6% by weight, of treatment composition on fiber, based on the total weight of the fiber.

In one embodiment of the invention, a sheet of caustic treated fibers or conventional fibers in roll form is conveyed through a treatment zone where the treatment composition is applied on both surfaces by conventional methods such as spraying, rolling, dipping, knife-coating or any other manner of impregnation. A preferred method of applying the treatment composition solution to the fiber in roll form is by puddle press or size press.

In one embodiment of the present invention, the fiber in sheet or roll form, after having been treated with a solution of the treatment composition, then is preferably transported by a conveying device such as a belt or a series of driven rollers though a three-zone oven for drying and curing.

Fiber in fluff, roll, or sheet form after treatment with the solution of the treatment composition preferably is dried and cured in a two-stage process, and more preferably dried and cured in a one-stage process. Such drying and curing removes water from the fiber, thereupon inducing the formation of an ester linkage between hydroxyl groups of the cellulosic fibers and cross-linking agent. Any curing temperature and time can be used so long as they produce the desired effects described herein. Using the present disclosure, persons having ordinary skill in the art can determine suitable drying and curing temperatures and times, depending on the type of fiber, the type of treatment of the fiber, and the desired bonding density of the fiber.

Curing typically is carried out in a forced draft oven preferably from about 130° C. to about 225° C. (about 265° F. to about 435° F.), and more preferably from about 160° C. to about 220° C. (about 320° F. to about 430° F.), and most preferably from about 180° C. to about 215° C. (about 350° F. to about 420° F.). Curing is preferably carried out for a sufficient period of time to permit complete fiber drying and efficient bonding between cellulosic fibers and the treatment composition. Preferably, the fiber is cured from about 1 min to about 25 min, more preferably from about 7 min to about 20 min, and most preferably from about 8 min to about 15 min.

It is preferred that the cellulosic fiber is cured and dried in a one-step process, for a period of time ranging from about 3 minutes to about 15 minutes at temperatures within the range of 130° C. to about 225° C. Alternatively, the drying and curing may be conducted in a two-step process. In this case, the drying step dries the impregnated cellulosic fiber, and the dried cellulosic fiber then is cured to form intra-fiber bonds. In one embodiment where the curing and drying are carried out in a two-step process, the drying step is carried out at a temperature below the curing temperature (e.g., between room temperature and about 150° C.) before the curing step. The curing step is then carried out, for example, for about 1 to 10 minutes at a temperature within the range of 150° C. to about 225° C. Alternatively, the curing step may be carried out for about 0.5 minutes to about 5 minutes at a temperature range of about 130° C. to about 225° C.

In the case where the cross-linking is carried out on fiber in fluff form, the fiber preferably is treated initially with the treatment composition described herein while in roll or sheet form, dried at a temperature below curing temperature, defiberized by passing it through a hammermill or the like, and then heated at elevated temperatures to promote intra-fiber bond formation between fibers and the treatment composition. In an alternate embodiment, the cellulosic base fibers may be treated with the treatment composition while in fluff form and then dried and cured according to any of the methods described herein.

While not intending to being limited by theory of operation, curing the treated cellulosic fibers results in the formation of ester cross-links between the hydroxyl groups of the cellulosic fibers and the acid groups of the treatment composition. The ester cross-links can form between the hydroxyl groups of the same chain or between hydroxyl groups of closely located cellulosic chains. The reaction mechanism between hydroxyl groups of the cellulosic fibers and the treatment composition is expected to be similar to that between cellulose and conventional cross-linking agents such as, for example, alkane polycarboxylic acids. The mechanism of cross-linking cellulose with polycarboxylic acid has been described by Zhou et al., Vol. 58 of Journal of Applied Polymer Science, pp. 1523–1524 (1995) and by Lees, M. J., Vol. 90 (3) of The Journal of Textile Institute, pp. 42–49 (1999).

The cellulosic fibers modified in accordance with embodiments of the present invention preferably possess characteristics that are desirable in absorbent articles. For example, the acquisition fluff pulp preferably has a centrifuge retention capacity of less than about 0.6 grams of synthetic saline per gram of oven dried (OD) fibers (hereinafter "g/g OD"). The acquisition fluff pulp also has other desirable properties, such as absorbent capacity of greater than about 10.0 g/g OD, an absorbency under load of greater than about 8.0 g/g OD, less than about 10.0% of fines, and an acquisition rate upon the third insult (or third insult strikethrough) of less than about 11.0 seconds. The particular characteristics of the cellulosic based acquisition fiber can be determined in accordance with the procedures described in more detail in the examples.

The centrifuge retention capacity is a measure of the ability of the fiber to retain fluid against a centrifugal force. It is preferred that the acquisition fluff pulp have a centrifuge retention capacity of less than about 0.6 g/g OD, more preferably, less than about 0.55 g/g OD. The acquisition fluff pulp can have a centrifuge retention capacity as low as about 0.50 g/g.

The absorbent capacity is a measure of the ability of the fiber to absorb fluid without being subjected to a confining or restraining pressure. The absorbent capacity preferably is determined by the absorbency test method described herein. It is preferred that the acquisition fluff pulp of the invention has an absorbent capacity of more than about 8.0 g/g OD, more preferably, greater than about 9.0 g/g OD, even more preferably greater than about 10.0 g/g OD, and most preferably greater than about 11.0 g/g OD. The acquisition fluff pulp can have an absorbent capacity as high as about 13.0 g/g OD.

The absorbency under load is a measure of the ability of the fiber to absorb fluid against a restraining or confining force over a given period of time. It is preferred that the acquisition fluff pulp has an absorbency under load of greater than about 7.0 g/g OD, more preferably, greater than about 8.5 g/g OD, and most preferably, greater than about 9.0 g/g OD. The acquisition fluff pulp can have absorbency under load as high as about 11.0 g/g OD.

It also is preferred in embodiments of the present invention that the acquisition fluff pulp has a dry bulk of at least about 8.0 cm$^3$/g fiber, more preferably at least about 9.0 cm$^3$/g fiber, even more preferably at least about 10.0 cm$^3$/g fiber, and most preferably at least about 11.0 cm$^3$/g fiber.

The properties of the acquisition fluff pulp prepared in accordance with the embodiments described herein make the fiber suitable for use, for example, as a bulking material, in the manufacturing of high bulk specialty fiber that requires good absorbency and porosity. The acquisition fluff pulp can be used, for example, in non-woven, fluff absorbent products. The acquisition fluff pulp also may be used independently, or preferably incorporated with other cellulosic fibers to form blends using conventional techniques, such as air laying techniques. In an airlaid process, the acquisition fluff pulp, alone or in combination with other fibers, may be blown onto a forming screen or drawn onto the screen via a vacuum. Wet laid processes also may be used, combining the acquisition fluff pulp described herein with other cellulosic fibers to form sheets or webs of blends.

The acquisition fluff pulp of the embodiments may be incorporated into various absorbent articles, preferably intended for body waste management such as adult incontinent pads, feminine care products, and infant diapers. The acquisition fluff pulp can be used as an acquisition layer in the absorbent articles, and it can be utilized in the absorbent core of the absorbent articles. Towels and wipes and other absorbent products such as filters also may be made with the acquisition fluff pulp of the present invention. Accordingly, an additional feature of the embodiments is to provide an absorbent article and an absorbent core that includes the acquisition fluff pulp described herein.

In accordance with various embodiments of the present invention, the acquisition fluff pulp was incorporated into an acquisition layer of an absorbent article, and the acquisition time of the fiber in the absorbent article was evaluated by the Specific Absorption Rate Test (SART). The SART method is described in detail below. It was observed that absorbent articles that contained acquisition fluff pulp of the embodiments provided results comparable to those obtained by using commercial cross-linked fiber, especially those cross-linked in individualized form with polycarboxylic acids.

As previously mentioned, the acquisition fluff pulp could be used in an absorbent core of an absorbent article. The phrase "absorbent core" as used herein refers to a matrix of cellulosic wood fluff pulp that is capable of absorbing large quantities of fluid. Absorbent cores can be designed in a variety of ways to enhance fluid absorption and retention properties such as, for example, disposing superabsorbent materials amongst fibers of the wood pulp. The absorbent core may be used to manufacture consumer products such as diapers, feminine hygiene products or incontinence products.

A method of making an absorbent core may include forming a pad of acquisition fluff pulp or a mixture of acquisition fluff pulp and other fiber, and incorporating particles of superabsorbent polymer in the pad. The pad can be wet laid or airlaid. Preferably the pad is airlaid. It also is preferred that the SAP and acquisition fluff pulp, or a mixture of acquisition fluff pulp and cellulosic fiber are air-laid together.

The expressions "superabsorbent polymer" or "SAP" as used herein refer to a polymeric material that is capable of absorbing large quantities of fluid by forming a hydrated gel. Superabsorbent materials are well-known to those skilled in the art as substantially water-insoluble, absorbent polymeric compositions that are capable of absorbing large amounts of fluid ((0.9% solution of NaCl in water) and/or blood) in relation to their weight and forming hydrogel upon such absorption. Examples of superabsorbent polymers include a hydrolyzed starch-acrylonitrile graft copolymer, a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-cross-linking polyacrylic acid, a cross-linked polyacrylate salt, carboxylated cellulose, and a neutralized cross-linked isobutylene-maleic anhydride copolymer. An absorbent core may comprise any SAP known in the art. The SAP can be in the form of particulate matter, flakes, fibers and the like. Exemplary particulate forms include granules, pulverized particles, spheres, aggregates and agglomerates. Exemplary and preferred superabsorbent materials include salts of crosslinked polyacrylic acid such as sodium polyacrylate.

It is preferred in embodiments of the present invention that the acquisition fluff pulp is present in the absorbent core in an amount ranging from about 10% to about 80% by weight, based on the total weight of the core. More preferably, the acquisition fluff pulp is present in an absorbent core from about 20% to about 60% by weight.

The absorbent core may comprise one or more layers that may comprise acquisition fluff pulp. In one embodiment, one or more layers of the absorbent core comprise a mixture of acquisition fluff pulp with conventional cellulosic fibers and SAP. Preferably, the acquisition fluff pulp of the embodiments described herein is present in the fiber mixture in an amount ranging from about 1% to 70% by weight, based on the total weight of the fiber mixture, and more preferably present in an amount ranging from about 10% to about 40% by weight. Any conventional cellulosic fiber may be used in combination with the acquisition fluff pulp. Suitable conventional cellulosic fibers include any of the wood fibers mentioned previously herein, including caustic-treated fibers, rayon, cotton linters, and mixtures and combinations thereof.

In one embodiment of the invention, the absorbent core may have an upper layer comprising acquisition fluff pulp, and a lower layer comprising a composite of cellulosic fibers and superabsorbent polymer. In this embodiment, the upper layer has a basis weight of about 40 gsm to about 400 gsm. The upper layer and the lower layer of the absorbent core may have the same overall length and/or the same overall width. Alternatively, the upper layer may have a length that is longer or shorter than the length of the lower layer. Preferably, the length of the upper layer is 120% to 300% the length of the lower layer. The upper layer may have a width that is wider or narrower than the width of the lower layer. Preferably, the width of the upper layer is 80% the width of the lower layer.

Each layer of the absorbent core may comprise a homogeneous composition, where the acquisition fluff pulp is uniformly dispersed throughout the layer. Alternatively, the acquisition fluff pulp may be concentrated in one or more areas of an absorbent core layer. In one embodiment of the present invention, the single layer absorbent core contains a surface-rich layer of the acquisition fluff pulp. Preferably, the surface-rich layer has a basis weight of about 40 gsm to about 400 gsm. Preferably, the surface-rich layer has an area that is about 30% to about 70% of the total area of the absorbent core.

An absorbent core made in accordance with the embodiments preferably contains SAP in an amount of from about 20% to about 60% by weight, based on the total weight of the composite, and more preferably from about 30% to about 60% by weight, based on the total weight of the composite. The absorbent polymer may be distributed throughout an absorbent composite within the voids in the fiber. In another embodiment, the superabsorbent polymer may attached to acquisition fluff pulp via a binding agent that includes, for example, a material capable of attaching the SAP to the fiber via hydrogen bonding, (see, for example, U.S. Pat. No. 5,614,570, the disclosure of which is incorporated by reference herein in its entirety).

An absorbent core containing acquisition fluff pulp and superabsorbent polymer preferably has a dry density of between about 0.1 g/cm$^3$ and 0.50 g/cm$^3$, and more preferably from about 0.2 g/cm$^3$ to 0.4 g/cm$^3$. The absorbent core can be incorporated into a variety of absorbent articles, preferably those articles intended for body waste management, such as diapers, training pants, adult incontinence products, feminine care products, and toweling (wet and dry wipes).

In order that various embodiments of the present invention may be more fully understood, the embodiments will be illustrated, but not limited, by the following examples. No specific details contained therein should be understood as a limitation to the embodiments.

Test Methods:

Fiber Quality

Fiber quality evaluations were carried out on a Fluff Fiberization Measuring Instrument (Model 9010, Johnson Manufacturing, Inc., Appleton, Wis., USA). The Fluff Fiberization Measuring Instrument is used to measure knots, nits and fine contents of fibers. In this test, a sample of fiber in fluff form was continuously dispersed in an air stream. During dispersion, loose fibers passed through a 16 mesh screen (1.18 mm) and then through a 42 mesh (0.36 mm) screen. Pulp bundles that remained in the dispersion chamber ("knots") and those that were trapped on the 42-mesh screen ("accepts") were removed and weighed. The combined weight of these two was subtracted from the original weight of the fluff sample to determine the weight of fibers that passed through the 0.36 mm screen ("fines.")

ISO Brightness

ISO Brightness evaluations were carried out on various samples of the acquisition fluff pulp of the present invention, using TAPPI test methods T272 and T525. Selected samples of the acquisition fluff pulp in sheet form were defiberized by feeding them through a hammermill, and then about 3.0 g of the defiberized fluff was airlaid into a circular test sample having approximately a 60 mm diameter. The produced samples were then evaluated for ISO brightness.

The Absorbency Test Method

The absorbency test method was used to determine the absorbency under load, absorbent capacity, and centrifuge retention capacity of acquisition fluff pulp of the present invention. The absorbency test was carried as follows: The test was performed using a plastic cylinder with one inch inside diameter having a 100-mesh metal screen attached to the base of the cylinder. Into the cylinder was inserted a plastic spacer disk having a 0.995 inch diameter and a weighs about 4.4 g. The weight of the cylinder assembly was determined to the nearest 0.001 g ($W_0$), and then the spacer was removed from the cylinder and about 0.35 g (dry weight basis) of acquisition fluff pulp was air-laid into the cylinder. The spacer disk then was inserted back into the cylinder on the air-laid fibers, and the cylinder assembly was weighed to the nearest 0.001 g ($W_1$). Fibers in the cell were compressed with a load of 4.0 psi for 60 seconds, the load then was removed and the fiber pad was allowed to equilibrate for 60 seconds. The pad thickness was measured, and the result was used to calculate the dry bulk of acquisition fluff pulp.

A load of 0.3 psi then was placed on the spacer over the fiber pad and the pad was allowed to equilibrate for 60 seconds, after which the pad thickness was measured, and the result was used to calculate the dry bulk under load of the cellulosic based acquisition fibers. The cell and its contents then were hanged in a Petri dish containing sufficient amount of saline solution (0.9% by weight NaCl) to touch the bottom of the cell and the fiber was allowed to stay in contact with the saline solution for 10 minutes. Then it was removed and hanged in another empty Petri dish and allowed to drain for one minute. The load was removed and the weight of the cell and contents was determined ($W_2$). The weight of the saline solution absorbed per gram fibers then was calculated according to Equation (1) below, the result of which was expressed as the "absorbency under load" (g/g).

$$\frac{W_2 - W_1}{W_1 - W_0} \quad (1)$$

The absorbent capacity of the acquisition fluff pulp was determined in the same manner except that the experiment was carried under zero load. The results were used to determine the weight of the saline solution absorbed per gram fiber and expressed as the "absorbent capacity" (g/g).

The cell then was centrifuged for 3 minutes at 2400 rpm (Centrifuge Model HN, International Equipment Co., Needham HTS, USA), and the weight of the cell and contents is reported ($W_3$). The centrifuge retention capacity was then calculated according to Equation (2) below, the result of which was expressed as the "centrifuge retention capacity" (g/g).

$$\frac{W_3 - W_0}{W_1 - W_0} \quad (2)$$

Specific Absorption Rate Test (SART)

The SART test method evaluates the performance of the acquisition fibers in an absorbent article. To evaluate the acquisition property of the cross-linked fibers, the acquisition time is measured, which is the time required for a dose of saline to be absorbed completely into an absorbent article comprised of absorbent core and an acquisition layer.

Test samples in the SART test method are comprised of two layers: an acquisition layer and an absorbent core. In this test, a standard absorbent core was selected as a core sample for all test samples. An airlaid pad (120 gsm) made from the acquisition fibers of the present invention was used as an acquisition layer, superimposed on the core sample. The acquisition layer and the core sample were cut into a test sample having a circular shape with a 60 mm diameter. The test sample was placed into a testing apparatus (obtained from Portsmouth Tool and Die Corp., Portsmouth, Va., USA) consisting of a plastic base and a funnel cup. The base is a plastic cylinder having an inside diameter of 60.0 mm that is used to hold the sample. The funnel cup is a plastic cylinder having a hole with a star shape at the bottom, the outside diameter of which is 58 mm. The test sample was placed inside the plastic base, and the funnel cup was placed inside the plastic base on top of the test sample. A load of about 0.6 psi having a donut shape was placed on top of the funnel cup.

The apparatus and its contents were placed on a leveled surface and the sample was insulted with three successive doses of 9.0 ml of saline solution, (0.9% by weight NaCl), the time interval between doses being 20 minutes. The doses were added with a Master Flex Pump (Cole Parmer Instrument, Barrington, Ill., USA) to the funnel cup. The time (in seconds) required for the saline solution of each dose to disappear from the funnel cup was recorded and expressed as "acquisition time," or "strikethrough." The time required for the third dose to be absorbed completely by the test sample was recorded as the "third insult strikethrough time."

EXAMPLES

The following conventional wood fluff pulps were used in the following examples:

Rayfloc-J-LD®: conventional unplasticized wood fluff pulp, commercially available from the Rayonier mill at Jesup, Ga.

Rayfloc-JMX®: partially de-bonded wood fluff pulp commercially available from the Rayonier mill at Jesup, Ga.

Rayfloc-X-J®: fully de-bonded wood fluff pulp commercially available from the Rayonier mill at Jesup, Ga.

Example 1

This example illustrates one method suitable for synthesizing the anti-hydrogen-bonding agent poly(dimethylsiloxane), diglycidyl ether terminated-diethanolamine PDMS-DGE-DEA. Equi-equivalent quantities of diethanolamine (214.0 g, 2.04 equiv.) and poly(dimethylsiloxane), diglycidyl ether terminated (1.0 kg, 2.04 equiv.) were placed in round bottom flask (2.0 L) equipped with a magnet stir bar. The mixture was heated in a water bath (about 60° C.) for about 4 hours while stirring, after which a clear, thick liquid was obtained. The liquid was used as is in making treatment composition solution.

Example 2

This example illustrates a representative method for making an acquisition fluff pulp in sheet form. In addition, the effect of using various amounts of anti-hydrogen-bonding agent PDMSDGE-DEA on the fiber quality and the performance of the acquisition fluff pulp was evaluated.

Treatment composition solutions (1.0 L) containing citric acid (3.75 wt %), sodium hypophosphite (1.33 wt %), and various concentrations of PDMSDGE-DEA (0.5–0.15 wt %), were prepared. The pH of the solutions were adjusted to about 2.9 to 3.2 with an aqueous solution of NaOH (about 8.0 g, 50 wt %). The treatment composition solutions then were used to treat hand sheets of Rayfloc®-J-LD cut from a jumbo roll mad at Jesup Mill. The treatment was carried out as follows: a hand sheet of Rayfloc®-J-LD (a 12 inch×12 inch sheet with a basis weight of about 680 gsm (g/m²), obtained from a jumbo roll was dipped in the solution of treatment composition prepared above, then pressed to achieve the desired level of treatment composition solution (100% wet pick-up). The sheet was then dried and cured at about 190° C. The curing was carried out in an air driven laboratory oven for about 10 min to produce acquisition fluff pulp in sheet form. The acquisition fluff pulp sheet was then defiberized by feeding it through a hammermill (Kamas Mill H01, Kamas Industries AB, Vellinge, Sweden) and evaluated for fiber quality and absorbency the results are summarized in Tables 1 and 2 below.

TABLE 1

Absorbent properties of acquisition fluff pulp made as shown in Example 2 using Rayfloc ®-J-LD base fiber

| PDMSDGE-DEA (wt %) | Absorbent Capacity (g/g OD) | Absorbency Under Load (g/g OD) | Centrifuge Retention (g/g OD) |
|---|---|---|---|
| Rayfloc ®-J-LD[1] (no anti-hydrogen-bonding agent) | 9.1 | 7.8 | 0.53 |
| 0.05% | 12.2 | 10.5 | 0.58 |
| 0.10% | 11.0 | 9.3 | 0.53 |
| 0.15% | 12.1 | 9.4 | 0.53 |

[1]Conventional fiber cross-linked as shown in Example 2 using a cross-linking solution containing citric acid (3.2%), polymaleic acid (0.8%) and a catalyst $NaH_2PO_4$ (0.6%) solution, the pH of the solution was adjusted to about 3.0.

TABLE 2

Fiber quality of commercial fibers and acquisition fluff pulp prepared using treatment composition of Example 2

| PDMSDGE-DEA (wt %) | Knots and nits (%) | Fines (%) | ISO Brightness |
|---|---|---|---|
| Rayfloc ®-J-LD (untreated) | 6.2 | 5.1 | 86.0 |
| Commercial cross-linked fiber[1] | 29.0 | 4.0 | 75.0 |
| Rayfloc ®-J-LD[2] (no anti-hydrogen-bonding agent) | 44.4 | 7.7 | |
| 0.06% | 18.5 | 8.2 | 79.6 |
| 0.08% | 7.7 | 7.6 | 75.6 |
| 0.15% | 7.7 | 7.2 | 79.6 |

[1]Extracted from the acquisition layer in the Pampers ® Baby Dry product, produced by Procter & Gamble Company, Cincinnati, OH. This acquisition layer is representative of commercially-available individualized cross-linked cellulose fiber.
[2]Conventional fiber cross-linked as shown in Example 2 using a cross-linking solution containing citric acid (3.2%), polymaleic acid (0.8%) and a catalyst $NaH_2PO_4$ (0.6%) solution, the pH of the solution was adjusted to about 3.0.

The results in Table 2 demonstrate that samples treated with a treatment solution containing PDMSDGE-DEA have significantly lower knots and nits as compared to samples cross-linked without PDMSDGE-DEA and commercial fibers cross-linked in individualized form. Also as can been seen from the results unlike conventional debonding agents, PDMSDGE-DEA showed a positive effect on absorbent capacity and absorbency under load.

Example 3

Example 2 was repeated, except in this example no adjustment was made to the pH (~1.90) of the treatment composition solutions. Solutions with various concentrations of PDMSDGE-DEA were prepared and then used to treat hand sheets of Rayfloc®-J-LD as shown in Example 2. Fiber qualities and absorbent properties of the resultant acquisition fluff pulp are summarized in Tables 3 and 4.

TABLE 3

Absorbent properties of acquisition fluff pulp made in accordance with example 3 using Rayfloc ®-J-LD base fiber

| PDMSDGE-DEA (wt %) | Absorbent Capacity (g/g OD) | Absorbency Under Load (g/g OD) | Centrifuge Retention (g/g OD) |
|---|---|---|---|
| 0.05% | 11.3 | 9.5 | 0.57 |
| 0.10% | 11.2 | 9.2 | 0.53 |
| 0.15% | 11.2 | 9.3 | 0.52 |

TABLE 4

Fiber quality of commercial fibers and acquisition fluff pulp made in accordance with example 2

| PDMSDGE-DEA (wt %) | Knots and nits (%) | Fines (%) | ISO Brightness |
|---|---|---|---|
| Rayfloc ®-J-LD (untreated) | 6.2 | 5.1 | |
| 0.05% | 22.3 | 8.8 | 78.1 |
| 0.10% | 7.0 | 9.0 | 78.8 |
| 0.15% | 3.4 | 8.4 | 80.0 |

Example 4

This example illustrates the effect of using treatment compositions prepared using anti-hydrogen-bonding agent PDMSDGE-DEA (0.1%) and various cross-linking agents, on absorbent properties of representative acquisition fluff pulp formed in accordance with the present invention.

Three treatment composition solutions were prepared in accordance with the method described in Example 2. The solutions contained a cross-linking agent selected from glyoxylic acid, glyoxal, and a mixture of citric acid and polymaleic acid (in a ratio of 8:2 by weight). The treatment composition solutions were used to treat hand sheets of Rayfloc®-J-LD fibers, using the method described in Example 2. The treated fiber samples were cured and dried at 190° C. for about 10 minutes to produce acquisition fluff pulp samples. The samples were subsequently defiberized, using the method described in Example 2. Absorbent properties and fiber quality of the resultant acquisition fluff pulps were then evaluated, the results of which are presented in Tables 5 and 6.

TABLE 5

Absorbent properties of acquisition fluff pulp made in accordance with Example 4

| Cross-linking agent | Solution of Treatment Composition[1] Weight (%) of Cross-linking agent | Absorbent Capacity (0.3 psi) (g/g OD) | Absorbency Under Load (g/g OD) | Centrifuge Retention (g/g OD) |
|---|---|---|---|---|
| Glyoxylic acid | 2.5 | 10.2 | 8.5 | 0.49 |
| Glyoxal[2] | 3.0 | 10.6 | 8.1 | 0.55 |
| Citric acid/ polymaleic acid (8:2) | 4.0 | 11.6 | 9.9 | 0.54 |

[1]Solutions of treatment composition contain, in addition to the cross-linking agent, 0.1% by weight PDMSDGE-DEA.
[2]In case were glyoxal was used as cross-linking agent, curing was performed at about 150° C. for about 15 min, $MgCl_2$ (0.3%) was used as a catalyst

TABLE 6

Fiber quality of acquisition fluff pulp
made in accordance with Example 4

Composition of Treatment Composition Solution

| Cross-linking agent | Weight (%) of Cross-linking agent | Knots and nits (%) | Fines (%) |
| --- | --- | --- | --- |
| Glyoxylic acid | 2.5 | 5.8 | 9.2 |
| Glyoxal | 3.0 | 7.7 | 7.0 |
| Citric acid/polymaleic acid (8:2) | 4.0 | 6.8 | 8.6 |

Example 5

Acquisition fluff pulp made in accordance with an embodiment of the present invention was tested for liquid acquisition properties using the SART test method described above. The results are compared to those obtained from acquisition fiber made from wood pulp fibers treated with conventional de-bonding agents and cross-linked in accordance with the method shown in Example 2.

The absorbent core used in this experiment was obtained from commercially available absorbent material (NovaThin®, from Rayonier, Inc.), having a basis weight of about 780 gsm and containing about 40% by weight SAP. The core layer weighed about 2.4 g (±0.1 g). Acquisition layers were produced from air-laid pads of selective acquisition fluff pulp of the present invention. A control sample was produced having an air-laid acquisition layer comprising conventional Rayfloc J-LD pulp fiber. Each acquisition layer consisted of a 0.68 g air-laid pad compacted to a density of about 0.08 g/cm$^3$. The third insult strikethrough time for each test sample was recorded, and is provided in Table 7 below.

TABLE 7

Liquid acquisition time for absorbent articles containing
representative acquisition fluff pulps of the present
invention and conventional fiber

| Acquisition Fluff pulp/method of preparation | 3$^{rd}$ Insult Strikethrough (sec) |
| --- | --- |
| Control[1] | >45 |
| Rayfloc ®-J-LD[2] | 16.6 |
| Rayfloc ®-J-MX[2] | 21.0 |
| Rayfloc ®-X-J[2] | 36.2 |
| Example 1, citric acid (3.75%), PDMSDGE-DEA (0.5%) | 7.5 |
| Example 1, citric acid (3.75%), PDMSDGE-DEA (0.1%) | 9.6 |
| Example 1, citric acid (3.75%), PDMSDGE-DEA (0.15%) | 10.2 |
| Example 2, citric acid (3.75%), PDMSDGE-DEA (0.05%) | 10.0 |

[1]Rayfloc ®-J-LD (untreated)
[2]Conventional fiber cross-linked as shown in Example 2 using a cross-linking solution containing citric acid (3.2%), polymaleic acid (0.8%) and a catalyst NaH$_2$PO$_4$ (0.6%) solution.

The results in Table 7 show that the acquisition fluff pulp of the present invention has a significant affect on the acquisition rate of the absorbent core as compared to conventional untreated fluff pulp. The results in Table 7 also show that anti-hydrogen-bonding agents of the present invention have a negligible affect on acquisition properties of acquisition fiber of the present invention as compared to conventional de-bonding agents.

Example 6

Acquisition fluff pulp made in accordance with various embodiments of the present invention was evaluated for acquisition and rewet properties. The acquisition and rewet test measures the rate of absorption of multiple fluid insults to an absorbent product and the amount of fluid which can be detected on the surface of the absorbent structure after its saturation with a given amount of saline while the structure is placed under a load of 0.5 psi. This method is suitable for all types of absorbent materials, especially those intended for urine-absorption applications.

Acquisition and rewet for acquisition fluff pulp of the present invention were determined using standard procedures well known in the art with slight modification. Test samples were prepared from a commercially available absorbent core NovaThin®, from Rayonier, Inc., having a basis weight of about 805 gsm and containing about 40% by weight SAP, superposed with an acquisition layer having a basis weight of about 240 gsm prepared from an airlaid pad of acquisition fluff pulp fibers of the present invention. The acquisition layers were prepared as 25 cm×10 cm panels. The core samples were prepared as 40 cm×12 cm panels. Initially, the dry weight of a test sample was recorded. Then the sample was insulted with an 100 mL, fixed volume amount of saline solution (0.9% by weight NaCl), through a fluid delivery column at a 1 inch diameter impact zone under a 0.1 psi load. The time (in seconds) for the entire 100 mL of solution to be absorbed was recorded as the "acquisition time." Then the test sample was left undisturbed for a 30 minute waiting period. This entire procedure was repeated 2 more times on the same wet test specimen and in the same position as before. After the third insult was performed, a previously weighed a stack of filter paper (e.g., 15 sheets of Whatman #4 (70 mm)) was placed over the insult point on the test sample, and a 0.5 psi load (2.5 kg) was then placed on top of the stack of filter papers on the test sample for 2 minutes. The wet filter papers were then removed, and the wet weight was recorded. The difference between the initial dry weight of the filter papers and final wet weight of the filter papers was recorded as the "rewet value" of the test specimen. All results are summarized in Table 8 below.

TABLE 8

Acquisition and Rewet for absorbent articles[1] with acquisition layers
comprised of acquisition fluff pulps of the present invention

| Sample | Acquisition Time (sec) | | | Rewet |
| --- | --- | --- | --- | --- |
| (Acquisition Layer) | 1$^{st}$ insult | 2$^{nd}$ insult | 3$^{rd}$ insult | (g saline) |
| Control 1[1] | 45.0 | 20.7 | 26.1 | 7.2 |
| Control 2[2] | 34.0 | 23.9 | 28.6 | 6.0 |
| A[3] | 26.3 | 19.8 | 25.3 | 1.8 |
| B[4] | 29.0 | 20.6 | 25.9 | 4.8 |

[1]No acquisition layer was used in the control sample.
[2]Rayfloc ®-J-LD fluff was used in this experiment as an acquisition layer.
[3]Made in accordance with example 2 using 0.10% PDMSDGE-DEA.
[4]Made in accordance with example 2 using 0.15% PDMSDGE-DEA The results in Table 8 demonstrate that the treatment composition of the present invention positively impacted acquisition/distribution properties of the absorbent core. As can be seen from Table 8 the acquisition fluff pulps of the present invention reduced the acquisition times and rewet amounts when compared to a control without an acquisition layer and a control with an acquisition layer made from conventional untreated wood fiber.

While the invention has been described with reference to particularly preferred embodiments and examples, those skilled in the art recognize that various modifications may be made thereto without departing from the spirit and scope thereof.

What is claimed is:

1. A treatment composition for making acquisition fluff pulp, comprising a mixture of a cross-linking agent and an anti-hydrogen-bonding agent;
wherein the cellulosic fiber cross-linking agent is a polycarboxylic acid comprising a combination of polymeric polycarboxylic acid and alkanepolycarboxylic acid.

2. A treatment composition for making acquisition fluff pulp, comprising a mixture of a cross-linking agent and an anti-hydrogen-bonding agent; wherein the cross-linking agent is an aldehyde selected from the group consisting of: formaldehyde, glyoxal, glyoxylic acid, glutaraldehyde, glyceraldehydes, and combinations and mixtures thereof.

3. A treatment composition for making acquisition fluff pulp, comprising a mixture of a cross-linking agent and an anti-hydrogen-bonding agent;
wherein the cellulosic fiber cross-linking agent is a urea-based derivative selected from the group consisting of: urea based-formaldehyde addition products, methylolated ureas, methylolated cyclic ureas, methylolated lower alkyl cyclic ureas, methylolated dihydroxy cyclic ureas, dihydroxy cyclic ureas, lower alkyl substituted cyclic ureas, dimethyldihydroxy urea (1.3-dimethyl-4, 5-dihydroxy-2-imidazolidinone), dimethyldihydroxy urea (bis[N-hydroxymethyl]urea), dihydroxyethylene urea (4,5-dihydroxy-2-imidazolidinone), dimethylolethylene urea (1,3-dihydroxymethyl-2-imidazolidinone), glyoxal adducts of urea, polyhydroxyalkyl urea, hydroxyalkyl urea, β-hydroxyalkyl amide, and combinations and mixtures thereof.

4. The treatment composition of claim 1, wherein the anti-hydrogen-bonding agent is a silicon polymer terminated with at least one quaternary amine functional group.

5. The treatment composition of claim 2, wherein the anti-hydrogen-bonding agent is a silicon polymer terminated with at least one quaternary amine functional group.

6. The treatment composition of claim 3, wherein the anti-hydrogen-bonding agent is a silicon polymer terminated with at least one quaternary amine functional group.

7. The treatment composition of claim 1, wherein the cross-linking agent and the anti-hydrogen-bonding agent are mixed in a weight ratio of from about 1:1 to about 100:1.

8. The treatment composition of claim 2, wherein the cross-linking agent and the anti-hydrogen-bonding agent are mixed in a weight ratio of from about 1:1 to about 100:1.

9. The treatment composition of claim 3, wherein the cross-linking agent and the anti-hydrogen-bonding agent are mixed in a weight ratio of from about 1:1 to about 100:1.

10. The treatment composition of claim 1, wherein the alkane polycarboxylic acid is selected from the group consisting of: 1,2,3,4-butanetetracarboxylic acid, 1,2,3-propanetricarboxylic acid, oxydisuccinic acid, citric acid, itaconic acid, maleic acid, tartaric acid, glutaric acid, iminodiacetic acid, citraconic acid, tartrate monsuccinic acid, benzene hexacarboxylic acid, cyclohexanehexacarboxylic acid, and mixtures and combinations thereof.

11. The treatment composition of claim 1, wherein the polymeric polycarboxylic acid is prepared from one or more monomers selected from the group consisting of: acrylic acid, vinyl acetate, maleic acid, maleic anhydride, carboxy ethyl acrylate, itanoic acid, fumaric acid, methacrylic acid, crotonic acid, aconitic acid, acrylic acid ester, methacrylic acid ester, acrylic amide, methacrylic amid, butadiene, styrene, and combinations and mixtures thereof.

12. The treatment composition of claim 1, wherein the anti-hydrogen bonding agent is a quaternary amine terminated silicon polymer selected from formula I or II:

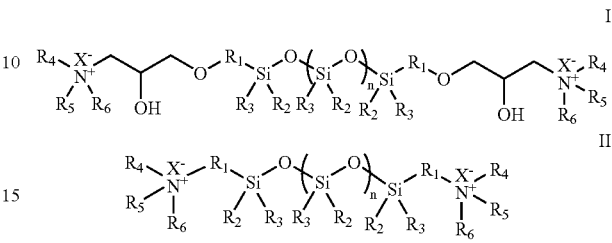

wherein $R_1$ represents a divalent alkyl group having two or more carbon atoms, said divalent alkyl group being linear, branched or cyclic;

wherein $R_2$ and $R_3$ each independently represent a hydrogen atom or an alkyl group with one or more carbon atoms;

wherein $R_4$, $R_5$ and $R_6$ each independently represent a hydrogen atom or an organic group selected from the group consisting of: alkyl, aryl, alkoxy, alkaryl, substituted alkyl, cycloaliphatic, aromatic, and combinations and mixtures thereof;

wherein X is an anion; and wherein n represents the number of repeating units, and is a number from 10 to 200.

13. The treatment composition of claim 2, wherein the anti-hydrogen bonding agent is a quaternary amine terminated silicon polymer selected from formula I or II:

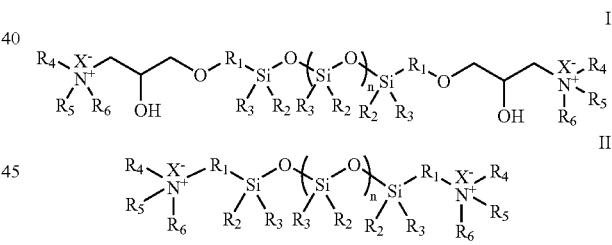

wherein $R_1$ represents a divalent alkyl group having two or more carbon atoms, said divalent alkyl group being linear, branched or cyclic;

wherein $R_2$ and $R_3$ each independently represent a hydrogen atom or an alkyl group with one or more carbon atoms;

wherein $R_4$, $R_5$ and $R_6$ each independently represent a hydrogen atom or an organic group selected from the group consisting of: alkyl, aryl, alkoxy, alkaryl, substituted alkyl, cycloaliphatic, aromatic, and combinations and mixtures thereof;

wherein X is an anion; and wherein n represents the number of repeating units, and is a number from 10 to 200.

14. The treatment composition of claim 3, wherein the anti-hydrogen bonding agent is a quaternary amine terminated silicon polymer selected from formula I or II:

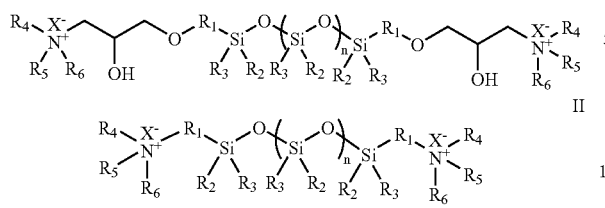

wherein R₁ represents a divalent alkyl group having two or more carbon atoms, said divalent alkyl group being linear, branched or cyclic;

wherein R₂ and R₃ each independently represent a hydrogen atom or an alkyl group with one or more carbon atoms;

wherein R₄, R₅ and R₆ each independently represent a hydrogen atom or an organic group selected from the group consisting of: alkyl, aryl, alkoxy, alkaryl, substituted alkyl, cycloaliphatic, aromatic, and combinations and mixtures thereof;

wherein X is an anion; and wherein n represents the number of repeating units, and is a number from 10 to 200.

15. The treatment composition of claim 12, wherein the quaternary amine terminated silicon polymer of formula I prepared by reacting epoxy terminated polysiloxane with at least one organic amine.

16. The treatment composition of claim 13, wherein the quaternary amine terminated silicon polymer of formula I is prepared by reacting epoxy terminated polysiloxane with at least one organic amine.

17. The treatment composition of claim 14, wherein the quaternary amine terminated silicon polymer of formula I is prepared by reacting epoxy terminated polysiloxane with at least one organic amine.

18. The treatment composition of claim 15, wherein the organic amines are aliphatic linear, branched or cyclic amines containing at least one primary, secondary or tertiary amino group.

19. The treatment composition of claim 16, wherein the organic amines are aliphatic linear, branched or cyclic amnines containing at least one primary, secondary or tertiary amino group.

20. The treatment composition of claim 17, wherein the organic amines are aliphatic linear, branched or cyclic amines containing at least one primary, secondary or tertiary amino group.

21. The treatment composition of claim 18, wherein the organic amines are secondary amines comprising at least one hydroxyl group.

22. The treatment composition of claim 19, wherein the organic amines are secondary amines comprising at least one hydroxyl group.

23. The treatment composition of claim 20, wherein the organic amines are secondary amines comprising at least one hydroxyl group.

24. The treatment composition of claim 18, wherein the organic amines are selected from the group consisting of diethylamine, ethanolamine, diethanolantine, bis-2-hydroxypropylarnine, bis-3-hydroxypropylantine, triethanolamine, tris-2- hydroxypropylamine, N-methylethanolamine, N-benzylethanolamine, N,N-dimethylethanolainine, piperidine, and morpholine.

25. The treatment composition of claim 19, wherein the organic amines are selected from the group consisting of diethylamine, ethanolamine, diethanolainine, bis-2-hydroxypropylaznine, bis-3-hydroxypropylamine, triethanolamine, tris-2- hydroxypropylainine, N-methylethanolamine, N-benzylethanolamine, N,N-dimethylethanolamine, piperidine, and morpholine.

26. The treatment composition of claim 20, wherein the organic amines are selected from the group consisting of diethylamine, ethanolainine, diethanolamine, bis-2-hydroxypropylamine, bis-3-hydroxypropylamine, triethanolamine, tris-2- hydroxypropylamine, N-methylethanolamine, N-benzylethanolamine, N,N-dimethylethanolamine, piperidine, and morpholine.

27. The treatment composition of claim 15, wherein the organic amines and epoxy terminated polysiloxane are reacted in stoichiometric proportions based on equivalent weight.

28. The treatment composition of claim 16, wherein the organic amines and epoxy terminated polysiloxane are reacted in stoichiometric proportions based on equivalent weight.

29. The treatment composition of claim 17, wherein the organic amines and epoxy terminated polysiloxane are reacted in stoichiometric proportions based on equivalent weight.

30. The treatment composition of claim 27, wherein the reaction is conducted at room temperature to about 100 °C. for about six to twenty hours.

31. The treatment composition of claim 28, wherein the reaction is conducted at room temperature to about 100 °C. for about six to twenty hours.

32. The treatment composition of claim 29, wherein the reaction is conducted at room temperature to about 100 °C. for about six to twenty hours.

* * * * *